United States Patent [19]

Razulis

[11] 4,125,376
[45] Nov. 14, 1978

[54] METHOD FOR DETECTING WATER POLLUTANTS
[75] Inventor: Marie K. Razulis, Randallstown, Md.
[73] Assignee: The United States of America as represented by the Secretary of the Army, Washington, D.C.
[21] Appl. No.: 789,768
[22] Filed: Apr. 22, 1977
[51] Int. Cl.² .................. B01L 3/14; G01N 33/18
[52] U.S. Cl. .................... 23/230 R; 23/230 M; 206/210; 206/569; 422/56; 422/57
[58] Field of Search ............... 23/230 R, 253 R, 259, 23/292, 230 M; 206/210, 569

[56] References Cited
U.S. PATENT DOCUMENTS

| 2,929,687 | 3/1960 | Buchoff | 23/292 X |
|---|---|---|---|
| 3,115,460 | 12/1963 | McCormick | 23/259 X |
| 3,206,602 | 9/1965 | Eberle | 23/253 R UX |
| 3,554,700 | 1/1971 | Maxon | 23/259 X |
| 3,741,727 | 6/1973 | Stroterhoff | 23/253 R X |
| 3,790,345 | 2/1974 | Mansfield et al. | 23/230 R |
| 3,876,378 | 4/1975 | Montagnon | 23/253 R |

OTHER PUBLICATIONS

F. Feigl, Spot Tests, vol. 1, Inorganic Applications, 4th ed., pp. 67-71 (1954).

Primary Examiner—Joseph Scovronek
Attorney, Agent, or Firm—Nathan Edelberg; Kenneth P. Van Wyck

[57] ABSTRACT

An improved method for identification and qualitative determination of potentially harmful pollutants in water through the use of a novel sampling test tube apparatus which consists essentially of a test tube containing a foam cube which has been impregnated with a detection chemical solution selected to react colorimetrically with specific pollutants to be detected.

14 Claims, 1 Drawing Figure

U.S. Patent     Nov. 14, 1978     4,125,376
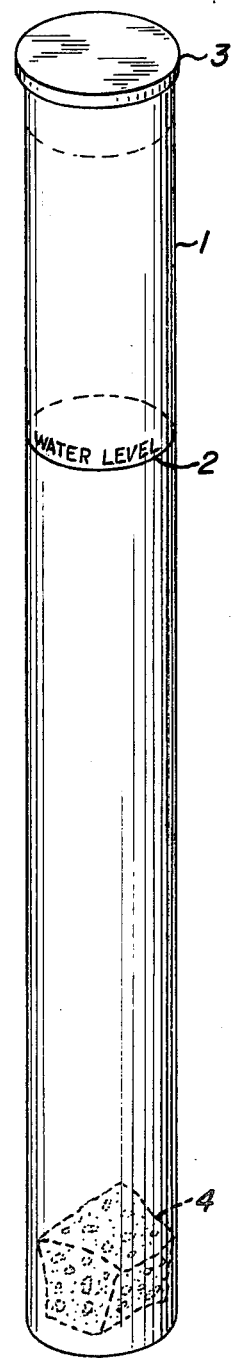

METHOD FOR DETECTING WATER POLLUTANTS

DEDICATORY CLAUSE

The invention described herein may be manufactured, used, and licensed by or for the Government for governmental purposes without the payment to me of any royalty thereon.

DESCRIPTION OF THE INVENTION

The invention relates to an improved method for identifying and qualitative determination of water pollutants which are potentially harmful.

The invention further relates to a simple, self-contained sampling tube test apparatus for detecting chemical and biological compounds in water during field tests and yet which gives rapid, sensitive and specific results when used by non-technically trained personnel.

The present methods of water testing for pollutants require wet chemical analytical techniques utilizing trained personnel to perform even the most routine analysis. The wet chemical analysis methods suffer from a number of disadvantages including time consuming and often complicated additional steps in preliminary separation and preparation of the test sample including a number of procedural steps such as concentration of the test sample, filtering, adjusting the pH and adding one or more reagents. The results obtained by the present methods thus depend on the technique and experience of the analyst, with a knowledge of chemistry and/or training being required, and the strict control of laboratory procedures including measurement of reagents. For the above reasons, the present wet chemical analytical techniques have had no practical application to on-site testing of water samples.

The process and test apparatus of this invention has succeeded in providing a simple on-site analytical test procedure for rapid, sensitive and specific identification of water born substances. Moreover, the process of this invention can obtain more reproducible differentiation between known chemicals and biological compounds in water without the need for technically trained personnel.

The principal object of this invention is to provide a sensitive, specific and relatively simple process for rapid qualitative determination of pollutants in water.

A further object of this invention is to provide a simple and completely prepackaged test apparatus for determination of pollutants in waterways, on-site.

A still further object of this invention is to provide a standardized analytical method and test sample apparatus for detection of water pollutants which will yield reproducibly accurate results when used by non-technically trained personnel.

These and other objects of the invention will be apparent to those skilled in the art from the following detailed description of the invention.

The FIGURE in the drawing shows the sampling tube test apparatus of the invention.

In particular, the test tube apparatus of this invention, as shown in the figure, consists of a transparent shell container 1, made for example of clear flexible plastic 1 cm. diameter by 9 cm in outside length with a marking 2, on the circumferential outside surface thereof, to indicate the required test water level, e.g., a distance of 3 cm from the top of the above 9 cm container would give a water volume of 5 ml. Disposed within the container 1 is a urethane foam cube 4 which is impregnated with a specific spot detection chemical for producing a colorimetric indication when exposed to specific pollutants in a tested water sample. The shell container is sealed from the surrounding atmosphere by use of a plug 3, made typically from natural polyethylene.

In operation, the water to be tested for pollutants is added to the shell container 1 until the shell container is filled to the water level mark 2. The shell container is then stoppered with plug 3 and the container is then shaken. A resulting color change on the detection chemical impregnated foam cube 4, indicates the presence of a particular pollutant in the tested water. The particular color change noted is compared to a color comparator chart of the specific element, compound or class of compounds present as pollutants in the water. The color change can also be used to give an estimate of the lower limit of the chemical or biological compound in water, thus yielding a semi-quantitative determination of the amount of compound present.

The method and test sample tube apparatus of this invention can be adapted to most spot test procedures, such as those disclosed in Feigl, F. and Anger, V., *Spot Tests in Organic Analysis*, Elsevier Publishing Company 1966 and Feigl, F. and Anger, V., *Spot Tests in Inorganic Analysis*, Elsevier Publishing Company, 6th Edition, 1972, as well as other wet chemical methods as disclosed in the publication of the American Public Health Association, *Standard Methods For The Examination Of Water And Wastewater*, of 1971 and Leith, W., *The Analysis of Organic Pollutants in Water and Wastewater*, Ann Arbor Science Publishers, Inc., 1973.

The urethane foam cubes impregnated with specific detecton chemicals used in the method and apparatus of this invention are prepared initially for impregnating by the following precedure;

Urethane foam cubes, cut 1 cm on edge, were of open cell type polyether. Before using, the cubes were washed by squeezing with 10% HCl in a plastic bag, followed by rinsing with distilled de-ionized water until free of chloride ion. Excess water was removed by squeezing the cubes with acetone and drying at 75° C. for about 1 hour.

The specific detection chemical used to impregnate the above washed foam cubes is dependent upon the particular pollutants or class of pollutants to be detected. Pollutants which are of particular concern in evaluating the water quality in this country include industrial chemicals, fertilizers, herbicides, pesticides and fungicides, particularly the hazardous heavy metal compounds and phenols. One detection chemical which can be used in this invention is a solution of dithizone (diphenylthiocarbazone) in di-isobutyl phthalate which has been found to be an effective indicator of hazardous heavy metals when used as the impregnate in the foam cubes of this invention. Phenols having a free phenol hydroxyl group can be detected by this invention through use of a detection composition containing amino antipyrene, bis (hydroxymethyl) amino methane and potassium ferricyanide in dimethylphthalate and acetone (the acetone was allowed to evaporate off of the impregnated cube). However, phenols whose reaction is inhibited by substitution in para position to the phenol hydroxyl group or nitro substitution in the ortho position are not detected.

The process of this invention can be best shown by reference to the following examples, which are meant to be merely illustrative and not in any way limiting to this invention.

EXAMPLE

Spot Test and Sampling Tube for Detecting Hazardous Heavy Metal Compounds

A solution of dithizone, (diphenylthiocarbazone, $C_6H_5NHNHCSN.NC_6H_5$) was prepared by dissolving 0.025 gr. dithizone in 50 ml of di-isobutyl phthalate. Washed urethane foam cubes (prepared or described above) were impregnated by placing 1.0g cubes and 3ml of dithizone solution in a plastic bag and kneading until a uniform color developed on the cube. Excess solution was removed by blotting with sheets of whatman filter paper to give a finished cube of bright green color.

A 2ml sample of water was collected in the sample tube. The sample tube, which is prepackaged with the impregnated foam cube, is then stoppered, shaken by hand for 40-60 seconds and any resulting color change in the bright green foam cube is noted. A positive test for the presence of heavy metal pollutants is indicated by a pink, red, yellow or amber color, while a grey color is a borderline indication. The compounds tested included such classes as industrial chemicals, fertilizers, herbicides, pesticides, and fungicides which are of concern to the United States Environmental Protection Agency. The compounds used to test the detection capabilities of the sampling tube were prepared in concentrations of 1000, 100, 10 and 1 mg/l 1 in distilled water, in Susquehanna River water (North Central Maryland) and Big Gunpowder Falls water (near city of Baltimore, MD).

The cubes responded to the following hazardous materials in the stated amounts: calcium hypochlorite, bleached white by 1 mg/1; lead arsenate, detecting 1000 mg/1 liter and phenylmercuric chloride, detecting 10 mg/liter. These results accurately reflected those found by conventional chemical analytic methods.

The instant process was further evaluated by testing the spot test and sampling tubes with solutions of specific metal compounds made up in distilled-deionized water in concentrations of 0.1 mg/l., 1.0 mg/l., 10 mg/1 and 100 mg/l. The results of the positive test are given in the following Table:

| Test Solution | Lowest Limit of Detection (in micrograms) | Positive Test Color |
|---|---|---|
| Chromium Compounds | | |
| Chromium Oxide ($CrO_3$) | 200 μg | Pinkish-yellow |
| Potassium Dichromate ($K_2Cr_2O_7$) | 200 μg | Pinkish-yellow |
| Cadmium Compounds | | |
| Cadmium Bromide($CdBr_2$) | 2 μg | Pinkish-white |
| Cadmium Nitrate($Cd(NO_3)_2$) | 200 μg | Orange |
| Cadmium Sulfate($CdSO_4$) | 0.2 μg | Pinkish-white |
| Cobalt Compounds | | |
| Cobalt Bromide($CoBr_2$) | 200 μg | Pink |
| Cobalt Nitrate $Co(NO_3)_2$ | 200 μg | Greyish-pink |
| Cobalt Sulfate($CoSO_4$) | 200 μg | Pink |
| Copper Compounds | | |
| Cupric Bromide ($CuBr_2$) | 1 μg | Pink |
| Cupric Acetate ($CU(CH_3COO)_2$) | 2 μg | Pale pink |
| Lead Compounds | | |
| Lead Chromate ($PbCrO_4$) | 200 μg | Pinkish-grey |
| Lead Thiocyanate ($Pb(SCN)_2$) | 2 μg | Pinkish-grey |
| Lead Sulfide (solid in water)($PbS$) | * | Pink |
| Lead Sulfate ($PbSO_4$) | 2 μg | Pinkish-grey |
| Mercury Compounds | | |
| Mercuric Bromide ($HgBr_2$) | 200 μg | Orange |
| Mercurous Chloride ($HgCl$) | 200 μg | Pink |
| Mercuric Chloride ($HgCl_2$) | 2 μg | Yellow-pink |
| Mercuric Iodide($HgI_2$) | 200 μg | Pink |
| Mercuric Thiocyanate ($Hg(SCN)_2$) | 200 μg | Pink-orange |
| Nickel Compounds | | |
| Nickel Acetate ($Ni(CH_3COO)_2$) | 200 μg | Pink |
| Silver Compounds | | |
| Silver Nitrate ($AgNO_3$) | 2 μg | Yellow |
| Zinc Compounds | | |
| Zinc Chloride ($ZnCl_2$) | 2 μg | Pinkish-grey |
| Zinc Oxide (solid in water) ($ZnO$) | * | Pink |
| Gold Compounds | | |
| Gold Chloride ($AuCl_3 . HCl . 4H_2O$) | 2 μg | Pink |

DETECTION OF METAL COMPOUNDS WITH HEAVY METAL SPOT TEST SAMPLING TUBES

* denotes negligible quantities due to low solubility in water

As shown from the above table, the spot test sampler tube and method of this invention applies to low concentrations, measured in parts per million, of a number of hazardous metal solutions. Though the table only shows the ten different metals tested and found to be detectable by this invention, dithizone is also sensitive to a number of other metals, as seen in Mellan, I. *Organic Reagents in Inorganic Analysis*, pages 91-93, Blackstone Company 1941.

EXAMPLE

Spot Test and Sampling Tube for Detecting Phenol Pollutants in Water

Washed urethane foam cubes (1 gr), prepared by the above washing procedure, are placed in a plastic bag with the following substances;

1 gr. Amino antipyrene
1 gr. Tis (hydroxymethyl) amino methane
3 ml. Dimethyl phthalate
3 ml. Acetone
0.1 gr. Potassium ferricyanide ($K_3Fe(CN)_6$)

and then kneaded until the cubes were uniform in appearance. The acetone was allowed to evaporate, producing a finished cube of pale yellow color.

In the test method, a water sample to be tested is added to the sampling tube, filling to the line, then stoppered and shaken for 5-10 seconds. A color change from pale yellow to orange (amber) or deep red indicates a positive test reaction. Using this procedure, a 5 ml sample of 10 mg/liter phenol solution gave a pink solution with amber-pink colored cube. Thus, the process of this invention provides a reliable method for detecting low levels of phenol.

The particular details of the construction of the sample tube apparatus of this invention are not critical in themselves and can be varied within the skill of one in the art.

The method and apparatus of this invention have allowed field testing of bodies of water for specific chemical or biological compounds by a simplified technique which yields rapid test response within a few minutes. The test sample tube apparatus of this invention is inexpensive to produce, disposable, readily transportable and non-hazardous to use, even when operated by non-technically trained personnel.

The essential features of this invention are that the test tube apparatus is completely pre-packaged, with all necessary detection chemicals within the foam cube, and do not require any pre-treatment of the water to be sampled. Further, the invention allows sampling and testing to be accomplished in the same apparatus, with a minimum of manipulative steps, thereby insuring uniform results which are easily reproducible. Finally, the testing method of this invention can be used under normal weather conditions experienced in the field, without resorting to open heating, and is not subject to external sources of contamination, e.g., unclean glassware due to its prepacked manufacture under controlled conditions.

Applicant having described her invention, obvious modifications will become apparent to those skilled in the related chemical art, and, therefore, applicant wishes to be limited only by the scope of the appended claims.

I claim:

1. A method for qualitatively determining the presence of specific pollutants selected from the group consisting of hazardous heavy metal compounds in water comprising the steps of providing a test sample tube containing a foam cube impregnated with a detection chemical solution which is selected to react with said (specific) pollutants, adding a sample of the water to be tested, stoppering and then shaking the tube to produce a colorimetric reaction, and noting the color change to indicate the presence of specific known pollutants.

2. The process of claim 1 wherein hazardous heavy metal compound pollutants are detected through use of a solution of dithizone diphenylthiocarbazone) in di-isobutyl phthalate as the detection chemical impregnate.

3. The process of claim 2 wherein the dithizone detection solution is present in a concentration of 0.025 grams in 50 ml of di-isobutyl phthalate.

4. The process of claim 1 wherein the heavy metal compounds detected comprise chromium, cadmium, cobalt, copper, lead, mercury, nickel, silver, zinc, gold, and calcium compounds.

5. The process of claim 4 wherein the metal pollutant detected is selected from the group consisting of lead, mercury and cadmium compounds.

6. A self-contained, prepackaged spot test tube apparatus for rapidly detecting the presence of specific pollutants in water consisting essentially of a shell container of transparent material with a line marking on the circumferential surface thereof, for indicating the desired water fill level, a urethane foam cube impregnated with a specific detection chemical solution of diphenylthiocarbazone in diisobutyl phthalate, for colorimetrically reacting with the specific pollutant to be detected and a stopper means.

7. The apparatus of claim 6 wherein the solution is 0.025 gr dithizone in 50 ml di-isobutyl phthalate.

8. The apparatus of claim 6 wherein the shell container is clear plastic of 1 cm diameter and 9 cm length, the stopper means is a natural polyethylene plug, and the fill line mark is placed 3 cm from the top to represent approximately 5 ml of water sample to be tested.

9. A method for qualitatively determining the presence of phenol pollutants, having a free phenol hydroxyl group whose reactivity is not inhibited by substitution in the para or ortho position, in water comprising the steps of providing a test sample tube containing of foam cube impregnated with a detection chemical which is selected to react with said pollutants, adding a sample of the water to be tested, stoppering and then shaking the tube to produce a colorimetric reaction, and noting the color change to indicate the presence of known phenol pollutants.

10. The process of claim 9 wherein phenol pollutants are detected through use of a mixture of amino antipyrene, bis (hydroxymethyl) amino methane and potassium ferricyanide in a dimethyl phthalate and acetone solution as the detection chemical impregnated in the cube.

11. The process of claim 10 wherein the detector chemical solution consists of 1 gram amino antipyrene, 1 gr. bis (hydroxymethyl) amino methane and 0.1 gr. potassium ferricyanide in 3 ml of dimethyl phthalate and 3.0 ml acetone.

12. A self-contained, prepackaged spot test tube apparatus for rapidly detecting the presence of specific pollutants in water consisting essentially of a shell container of transparent material with a line marking on the circumferential surface thereof, for indicating the desired water fill level, a urethane foam cube impregnated with a specific detection chemical solution of amino antipyrene, bis (hydroxymethyl) amino methane and potassium ferricyanide in dimethyl phthalate and acetone, for colorimetrically reacting with the specific pollutants to be detected and a stopper means.

13. The apparatus of claim 12 wherein the solution consists of 1 gr. amino antipyrene, 1 gr. bis (hydroxymethyl) amino methane and 0.1 gr. potassium ferricyanide in 3 ml of dimethyl phthalate and 3 ml of acetone.

14. The apparatus of claim 12 wherein the shell container is clear plastic of 1 cm diameter and 9 cm length, the stopper means is a natural polyethylene plug, and the fill line mark is placed 3 cm from the top to represent approximately 5 ml of water sample to be tested.

* * * * *